(12) United States Patent
Shopova et al.

(10) Patent No.: US 8,493,560 B2
(45) Date of Patent: Jul. 23, 2013

(54) PLASMONIC ENHANCEMENT OF WHISPERING GALLERY MODE BIOSENSORS

(75) Inventors: Siyka Shopova, Staten Island, NY (US); Stephen Arnold, New York, NY (US); Raaj Haresh Rajmangal, South Ozone Park, NY (US)

(73) Assignee: Polytechnic Institute of New York University, Brooklyn, NY (US)

( * ) Notice: Subject to any disclaimer, the term of this patent is extended or adjusted under 35 U.S.C. 154(b) by 162 days.

(21) Appl. No.: 13/205,756

(22) Filed: Aug. 9, 2011

(65) Prior Publication Data
US 2012/0069331 A1    Mar. 22, 2012

Related U.S. Application Data

(60) Provisional application No. 61/372,010, filed on Aug. 9, 2010.

(51) Int. Cl.
*G01J 3/44* (2006.01)

(52) U.S. Cl.
USPC ........ 356/301; 435/6.11; 435/7.1; 422/82.05; 422/82.11

(58) Field of Classification Search
USPC ................ 356/301, 317, 436, 440, 441, 442; 250/459.1, 214 R; 435/6.11, 4, 7.1, 7.9, 287.3, 435/287.9, 287.1; 422/82.05, 82.11
See application file for complete search history.

(56) References Cited

U.S. PATENT DOCUMENTS

| | | | | |
|---|---|---|---|---|
| 6,657,731 B2 * | 12/2003 | Tapalian et al. | ............... | 356/480 |
| 7,259,855 B2 * | 8/2007 | Fan et al. | ...................... | 356/436 |
| 2004/0137478 A1 * | 7/2004 | Arnold et al. | ..................... | 435/6 |
| 2010/0227315 A1 * | 9/2010 | Poetter et al. | ..................... | 435/6 |

* cited by examiner

*Primary Examiner* — Layla Lauchman
(74) *Attorney, Agent, or Firm* — John C. Pokotylo; Straub & Pokotylo

(57) ABSTRACT

A sensor for determining the presence or concentration of a target entity in a medium is described, and includes (a) an optical waveguide; (b) a microresonator optically coupled with the optical waveguide such that light within the optical waveguide induces a resonant mode within the microresonator at an equator region (or a mode volume); and (c) at least one plasmonic nanoparticle adsorbed onto a surface area of the microresonator within the equator region (or the mode volume) such that light inducing a resonant mode within the microresonator also causes a plasmonic resonance in the at least one plasmonic nanoparticle. Detection methods for using such sensors are also described. Finally, methods, involving the use of carousel forces, for fabricating such sensors are also described.

37 Claims, 9 Drawing Sheets the articles Y. Sun, X. D. Fan, *Anal. Bioanal. Chem.* 399, 205

PLASMONIC ENHANCEMENT OF WHISPERING GALLERY MODE BIOSENSORS

§0.2 RELATED APPLICATION

This application claims benefit to U.S. Provisional Application Ser. No. 61/372,010 (referred to as "the '010 provisional" and incorporated herein by reference), titled "SENSING ENHANCEMENT OF WHISPERING GALLERY MODE BIOSENSING BY PLASMON EXCITATION IN METAL NANOPARTICLES ON THE BIOSENSOR SURFACE," filed on Aug. 9, 2010, and listing Raaj Rajmangal and Siyka Shopova as the inventors. The scope of the present invention is not limited to any requirements of the specific embodiments in the '010 provisional.

§0.1 FEDERAL FUNDING

This invention was made with Government support and the Government may have certain rights in the invention as provided for by grant number 0933531 awarded by the National Science Foundation.

§1. BACKGROUND OF THE INVENTION

§1.1 Field of the Invention

The present invention concerns plasmonicly enhanced whispering gallery mode ("WGM") sensors that can detect the presence of, identify the composition of, and/or measure an amount or concentration of substances (referred to generally as "target entities," "target analytes," or simply "targets"), such as chemical or biological entities, even in amounts as small as a single protein particle as small as 3 nm (e.g., a "target entity"). The present invention also concerns methods and apparatus to make, and/or use such plasmonicly enhanced WGM sensors.

§1.2 Background Information

There exists an ongoing need for sensors for detecting various targets such as, for example, infectious agents (e.g., viruses, bacteria, etc.), toxins, small amounts of proteins, DNA, RNA, etc. Similarly, there exists an ongoing need for sensors for measuring DNA hybridization, protein adsorption, biomolecular mass, etc.

The need for fast and early detection of pathogens (e.g. viruses) and the antibodies that are generated as a biological response has led to the development of ultra-sensitive label-free biosensors that can detect individual bio-nanoparticles in aqueous solution. One known device used to detect the presence of small particles is a microsphere sensor coupled with an optical waveguide (e.g., an eroded optical fiber), one end of which is optically coupled with a light source and the other end with a light detector. Whispering gallery modes of the light circulating within the microsphere can be observed in optical signals detected at the detector. Examples of such WGM sensors are described in U.S. Pat. No. 7,491,491 (referred to as "the '491 patent" and incorporated herein by reference).

WGM sensors rely on the inherent sensitivity of the whispering gallery mode resonances within the resonator to changes in the external environment to provide a sensitive detection mechanism. Target entities selectively captured (e.g., adsorbed) by target receptors on the surface of the microsphere may shift the whispering gallery modes. These WGM sensors have emerged as an important optical tool for detection and analysis of trace quantities of biological materials. These WGM sensors have been employed in a host of applications including the detection of virus and bacteria, measurement of DNA hybridization and protein adsorption, and biomolecular mass determination.

However, known WGM sensors may have limits on the minimum size of the particles that may be detected and/or identified, and/or may be challenging to fabricate. More specifically, a detection signal produced by a single pathogen or biomolecule may depend on the volume of the particle, its electrical permittivity, the strength of the electric field at the particle position, etc. For viral-size particles adsorbed randomly on the surface of the resonator, this signal may approach or go well below the detection limit (also referred to as "limit of detection" or "LOD") of the sensor. In addition, the signal may vary considerably depending on where on the sensor the particle lands with respect to the maximum intensity ribbon of the WGM resonator. One way to compensate for the small particle size and the variations in the intensity of the detection signal is to increase the field at the particle position.

Moreover, in many WGM sensors, bulk chemical techniques are used to sensitize the resonator surface to the target entity. This can result in variations in the surface sensitivity to binding events, and thus lead to a corresponding variability of the measured signal during the transduction event. To eliminate such variations (which can impact, for example, a size determination of the target entity), it is advantageous if the target entities are captured at an optimal sensing region. For example, in spherical micro-resonators, the optimal sensing region of the surface corresponds to the equatorial perimeter about which the whispering gallery mode is stimulated. However, such localization of target receptors on the resonator surface is not possible with traditional bulk chemistry approaches.

Following the initial theory indicating that a WGM biosensor should be sensitive to a single virion in water. (See, e.g., the articles Y. Sun, X. D. Fan, *Anal. Bioanal. Chem.* 399, 205 (2011), and S. Arnold, M. Khoshsima, I. Teraoka, S. Holler, F. Vollmer, *Opt. Lett.* 28, 272 (2003), each incorporated herein by reference.) Influenza A has been detected on a microspherical silica resonator. (See, e.g., the article S. Arnold, R. Ramjit, D. Keng, V. Kolchenko and I. Teraoka, *Faraday Discuss.* 137, 65-83, discussion 99-113 (2007), incorporated herein by reference.) The WGM sensor is based on the idea that a nanoparticle entering the evanescent field of the WGM causes the mode to shift its frequency in reaction to being polarized by the field. The fractional shift in frequency $\Delta\omega_r/\omega_r$ is the negative of the energy required to polarize the particle, $W_p$, over that of the medium divided by the energy in the cavity $W_c$; $\Delta\omega_r/\omega_r = -W_p/W_c$. This simple rule, known as the Reactive Sensing Principle ("RSP"), has been shown to apply so long as the line width of the mode $\delta\omega_r$ is considerably larger than the shift mode $\Delta\omega_r$. (See, e.g., the articles, S. Arnold, R. Ramjit, D. Keng, V. Kolchenko and I. Teraoka, *Faraday Discuss.* 137, 65-83, discussion 99-113 (2007), F. Vollmer, S. Arnold, and D. Keng, *Proc. Natl. Acad. Sci. USA* 105, 20701 (2008), and S. I. Shopova, R. Rajmangal, Y. Nishida, S. Arnold, *Rev. Sci. Inst.* 81, 103110 (2010), each incorporated herein by reference.) For a Rayleigh particle, the RSP for the fractional frequency shift and the fractional shift in the free space wavelength tracking the mode, $\Delta\lambda_r/\lambda_r$, can be simply written as:

$$\frac{\Delta\omega_r}{\omega_r} = -\frac{\Delta\lambda_r}{\lambda_r} = -\frac{W_p}{W_c} \cong -\frac{\alpha_{ex}|E_0(r_v)|^2}{2\int\varepsilon_c|E_0(r)|^2 dV} \qquad (1)$$

where $\alpha_{ex}$ is the excess polarizability of the nanoparticle, $\in_c$ is the permittivity of the cavity, and $E_0(r_v)$ and $E_0(r)$ are modal field amplitudes at the position of the nanoparticle $r_v$ and throughout the mode, respectively. Since the energy required to polarize a nanoparticle is proportional to its polarizability $\alpha_{ex}$, the frequency shift is proportional to its mass m. It has been reported that the noise and mode volume limitations of a microspherical silica resonator have set the limit of detection in water to $m_{LOD}$~20 attogram (radius $\alpha_{LOD}$~17 nm). (See, e.g., the article, S. I. Shopova, R. Rajmangal, Y. Nishida, S. Arnold, *Rev. Sci. Inst.* 81, 103110 (2010), incorporated herein by reference.) To definitively detect single protein requires considerably better sensitivity ($m_{protein}$~0.1 attogram).

U.S. Patent Application Publication No. 2004-0137478 (referred to as "the '478 publication" and incorporated herein by reference), titled "ENHANCING THE SENSITIVITY OF A MICROSPHERE SENSOR," discusses increasing the sensitivity of WGM sensors. More specifically, the '478 publication describes creating a band (e.g., a narrow band) of target receptors such that the target receptors are substantially limited to a highly sensitive region near the equator of the microsphere (also referred to as the "equator region"). The '478 publication discusses fabricating microsphere sensors having target receptors substantially only at a sensitive equator region of a microsphere's surface by (i) selecting a microsphere with properties (refractive index ("RI") and radius) suited to the intended sensing application, (ii) optically coupling an eroded optical fiber with the microsphere at an equator, (iii) coating the microsphere with a UV reactive binding agent, such as an epoxy, (iv) selectively establishing an equator region with receptor material by immersing the microsphere in a solution with target receptors (e.g., of selected amines), and irradiating the equator band with UV light coupled into the microsphere through the eroded optical fiber causing a reaction between the target receptors in the solution and the binding agent, (v) washing the resulting sphere, and (vi) establishing the non-equator region as a non-interacting region (e.g., by immersing the microsphere in a solution of mono-secondary amines, irradiating the entire surface with UV light (e.g., from an external lamp) causing a reaction between the mono-secondary amines and any un-reacted binding agent, and washing). However, it would be useful to have WGM sensors that are easier to fabricate.

U.S. Patent Application Publication No. 2010-0297363 (referred to as "the '363 publication" and incorporated herein by reference), titled "FUNCTIONALIZING A SENSING RIBBON ON A WHISPERING GALLERY MODE MICRORESONATOR USING LIGHT FORCE TO FABRICATE A WHISPERING GALLERY MODE SENSOR" discusses using light force to fabricate WGM sensors including microresonators having target receptors selectively and substantially provided at only equator region (or mode volume) of the microresonators. More specifically, the '363 publication discusses fabricating microsphere sensors for determining the presence or concentration of a target entity in a medium by (i) immersing a microresonator in a solution including target receptors, (ii) inducing light to resonate within the microresonator, thereby generating an attractive force between a equator surface region of the microresonator and the target receptors in the solution, the attractive force being sufficiently strong to pull the target receptors close enough to the ribbon surface area of the microresonator to permit chemical forces to hold the target receptors to the ribbon surface area of the microresonator, wherein non-equator surface areas of the microresonator are substantially free of target receptors, and (iii) passivating the non-equator surface areas of the microresonator. However, it would be useful to increase the sensitivity of sensors described in the '363 publication.

Thus, there is a need to provide improved WGM sensors, preferably having an LOD capable of detecting a particle having a mass of ~0.1 attogram, and preferably being easier to fabricate.

§2. SUMMARY OF THE INVENTION

Exemplary embodiments consistent with the present invention may provide a sensor for determining the presence or concentration of a target entity in a medium, the sensor comprising: (a) an optical waveguide; (b) a microresonator optically coupled with the optical waveguide such that light within the optical waveguide induces a resonant mode within the microresonator at an equator region (or mode volume); and (c) at least one plasmonic nanoparticle adsorbed onto a surface area of the microresonator within the equator region (or mode volume) such that light inducing a resonant mode within the microresonator also causes a plasmonic resonance in the at least one plasmonic nanoparticle. In at least some embodiments consistent with the present invention, at least one receptor specific to the target entity is functionalized on the at least one plasmonic nanoparticle. In at least some embodiments consistent with the present invention, the plasmonic nanoparticle has a geometry selected from a group of geometries consisting of (A) nano-shell, (B) nano-rod, (C) non-concentric sphere, and (D) nano-dot, or consists of dimmers or several plasmonic particles placed in close proximity as a cluster. In at least some embodiments consistent with the present invention, the plasmonic nanoparticle is a metal selected from a group consisting of (A) Au, (B) Ag, (C) Cu, (D) Ti, and (E) Cr, or a semiconductor nanocrystal (quantum dot). In at least some embodiments consistent with the present invention, the sensor has a limit of detection ("LOD") on the order of 3 nm.

Such exemplary sensors may be produced by (a) placing a microresonator in a solution including at least one plasmonic nanoparticle; (b) inducing light to resonate within the microresonator, thereby (1) generating a resonant mode in association with the microresonator, and (2) attracting at least one plasmonic nanoparticle to the mode volume of the microresonator until the at least one plasmonic nanoparticle is adsorbed onto the surface within the mode volume of the microresonator. In at least some embodiments consistent with the present invention, surface areas of the microresonator other than the equator region are passivated. In at least some embodiments consistent with the present invention, the solution is a low conductivity solution selected from a group consisting of (A) water, (B) heavy water, and (C) a phosphate buffered saline solution. In at least some embodiments consistent with the present invention, the resonator selectively attracts only plasmonic nanoparticles that have positive polarizibilities at the wavelength of the light resonating within the microresonator.

Further, exemplary embodiments consistent with the invention may be used to determine the presence or concentration of a target entity in a medium by: (a) exposing a composite microresonator, including a dielectric microresonator and at least one plasmonic nanoparticle within the mode volume of the dielectric microresonator, to the medium; (b) inducing light to resonate within the microresonator, thereby (1) generating (A) a resonant mode in association with the dielectric microresonator and (B) a plasmonic resonance in the at least one plasmonic nanoparticle, and (2) attracting the target entity to at least one plasmonic nanoparticle of the composite microresonator; and (c) determining the presence, mass, or concentration of the target entity using a change in a characteristic of light exiting the composite microresonator.

In at least some embodiments consistent with the present invention, the act of determining the presence of the target entity can detect a target entity having a radius as low as 3 nm. In at least some embodiments consistent with the present invention, the act of determining the presence or concentration of the target entity using a change in a characteristic of light exiting the composite microresonator includes (i) identifying, from the light exiting the microresonator at a first time, a first waveform representing a benchmark resonance frequency in which the composite microresonator is free of the target entity, (ii) identifying, from the light exiting the microresonator at a second time which is after the first time, a second waveform shape indicating the adsorption of the target entity onto the at least one plasmonic nanoparticle, and (iii) comparing the second waveform with the first waveform. In at least some other embodiments consistent with the present invention, the act of determining the presence or concentration of the target entity using a change in a characteristic of light exiting the composite microresonator includes (i) identifying, from the light exiting the microresonator at a first time, a first waveform representing a benchmark resonance frequency in which the composite microresonator is free of the target entity, the first waveform including a first split resonant dip or peak having two branches, (ii) identifying, from the light exiting the microresonator at a second time which is after the first time, a second waveform shape indicating the adsorption of the target entity onto the plasmonic nanoparticle, the second waveform including a second split resonant dip or peak having two branches, and (iii) comparing the ratio of the relative intensities of the branches of the first split resonance dip or peak of the first waveform with the ratio of the relative intensities of the branches of the second split resonance dip or peak of the second waveform.

§3. BRIEF DESCRIPTION OF THE FIGURES

§4. DETAILED DESCRIPTION

The present invention may involve improved WGM sensors, improved methods and apparatus for determining the presence or concentration of a target entity in a medium using such improved WGM sensors, and/or methods for fabricating such improved WGM sensors and new methods of detecting the target entity. The following description is presented to enable one skilled in the art to make and use the invention, and is provided in the context of particular applications and their requirements. Thus, the following description of embodiments consistent with the present invention provides illustration and description, but is not intended to be exhaustive or to limit the present invention to the precise form disclosed. Various modifications to the disclosed embodiments will be apparent to those skilled in the art, and the general principles set forth below may be applied to other embodiments and applications. For example, although a series of acts may be described with reference to a flow diagram, the order of acts may differ in other implementations when the performance of one act is not dependent on the completion of another act. Further, non-dependent acts may be performed in parallel. Also, as used herein, the article "a" is intended to include one or more items. Where only one item is intended, the term "one" or similar language is used. In the following, "information" may refer to the actual information, or a pointer to, identifier of, or location of such information. No element, act or instruction used in the description should be construed as critical or essential to the present invention unless explicitly described as such. Thus, the present invention is not intended to be limited to the embodiments shown and the inventors regard their invention to include any patentable subject matter described.

Figure 1:
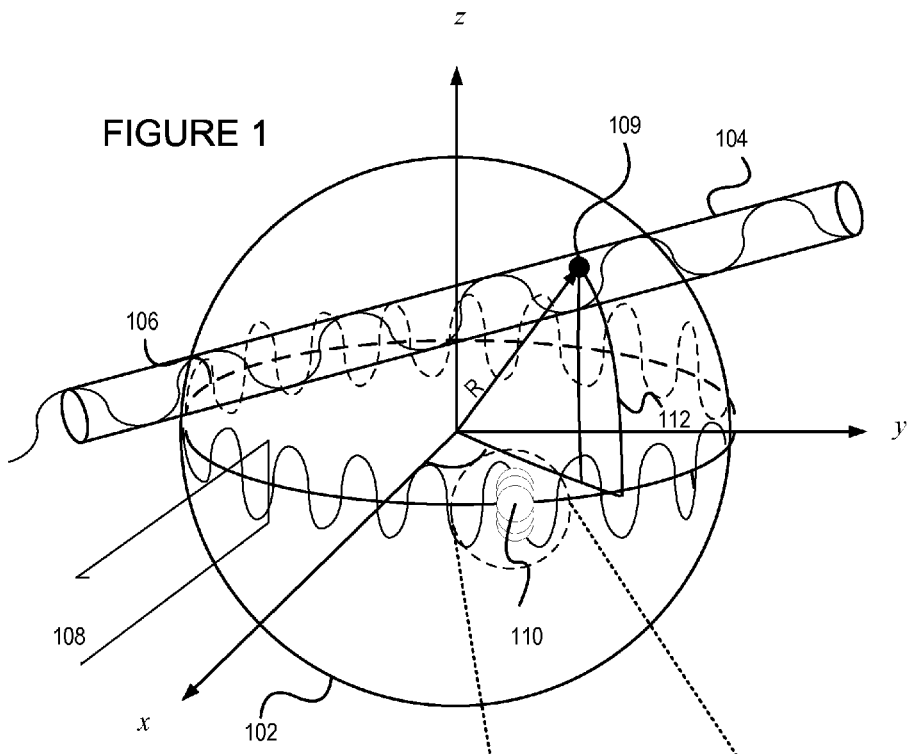
FIG. 1 illustrates an exemplary microsphere WGM sensor that may be fabricated in a manner consistent with the present invention.

§4.1 An Examplary Plasmonicly Enhanced Microsphere Sensor which May be Fabricated by Exemplary Techniques Consistent with the Present Invention FIG. 1 is an illustration of an exemplary microsphere sensor 100 which may be fabricated in a manner consistent with the present invention. A microsphere resonator 102 (also referred to more generally as a "microresonator" or simply "resonator") is optically coupled with an eroded optical fiber 104 (referred to more generally as a "waveguide") at a point or segment on an equator region 106 of the microsphere 102. (Note that the equator region 106 is defined by the light resonating within the microresonators. Therefore, even if a microresonator geometry has more than one equator, the "equator region" is defined by the "mode volume," not solely a function of the microresonator geometry.) In accordance with the present invention, a plasmonic (e.g., metallic) nanoparticle 110 has been adsorbed onto a surface area of the microsphere 102 on or adjacent to its equator region 106. By having the microsphere resonator 102 optically coupled with the optical waveguide 104, the light within the optical waveguide 104 induces a resonant mode within the microresonator 102 at the equator region 106, and the light inducing a resonant mode within the microresonator 102 also causes a plasmonic resonance in the plasmonic nanoparticle 110. In some embodiments consistent with the present invention, at least one receptor (specific to a target entity to be detected and/or measured) is provided on the plasmonic nanoparticle 110.

Figure 2:
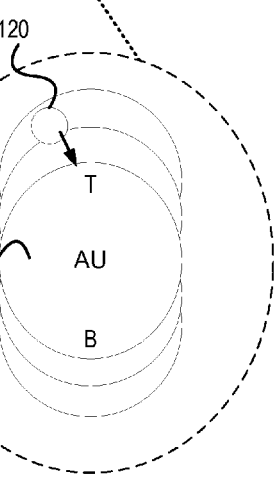
FIG. 2 illustrates details of a plasmonic nanoparticle at the equator of the microsphere WGM sensor of FIG. 1.

Exemplary sensors consistent with the present invention may increase the detection signal indicating individual targets, while also causing a preferential adsorption of the target onto a specific area on the resonator surface. Such exemplary sensors exploit the local field enhancement due to the excitation of plasmon resonance in the plasmonic nanoparticle 110. The spectral position of this plasmon resonance is determined by the type of material (Au, Ag, Cu, Ti, Cr, a quantum dot semiconductor (e.g., copper sulfide) nanocrystal, etc.), as well as the size and the shape (dot, rod, shell, concentric or non-concentric sphere, etc.) of the nanoparticle. When the plasmonic nanoparticle is placed at the highest evanescent intensity strip (that is the equator region) of a WGM resonator and excited by it, the local field of the WGM resonator-metal nanoparticle composite at the particle position will be greatly enhanced (e.g., $10^2$-$10^4$ times). (See, e.g., the article, Fuller, K A, Smith, D D, "Cascaded Photoenhancement from Coupled Nanoparticle and Microcavity Resonance Effects," *Optics Express*, 15, 3575 (2007), incorporated herein by reference.) According to the reactive sensing principle ("RSP") (See, e.g., the article, S. Arnold, M. Khoshsima, I. Teraoka, S. Holler and F. Vollmer, "Shift of Whispering Gallery Modes in Microspheres by Protein Adsorption," *Opt. Lett.*, 28, 272 (2003), incorporated herein by reference.) The shift of the resonance frequency is proportional to the intensity (field squared) at the point where a particle is adsorbed. RSP predicts an increase in the detection signal when the WGM and the plasmon resonance are at the same frequency. FIG. 2 illustrates the plasmon resonance of a plasmonic (e.g., Au) nanoparticle 110.

However, at frequencies very close to the plasmonic maximum, the plasmonic nanoparticle may become a heat source. Consequently, at such frequencies, forces of thermophoretic character may repel targets (e.g., bioparticles) away from the surface of the nanoparticle. Therefore, in some exemplary embodiments consistent with the present invention, the plasmonic nanoparticles are excited with a predetermined wavelength range that is (1) within the width of the plasmonic resonance, but (2) shifted from its maximum.

A dielectric microresonator provided with at least one plasmonic nanoparticle in its mode volume may be referred to as a "plasmonicly enhanced WGM sensor" or a "composite microresonator."

§4.1.1 Analytic Theory

Exemplary embodiments consistent with the present invention involve creating local plasmonic "hot spots" near the sensing equator region within the WGM's evanescent field. Plasmonic nanoparticles attached to the surface of a WGM resonator (though not solely at the equator region) have been shown to locally enhance the evanescent field without significantly degrading the quality factor, Q. (See, e.g., the article, S. I. Shopova, C. W. Blackledge, A. T. Rosenberger, *Appl. Phys.* B, 93, 183 (2008)), incorporated herein by reference.) In an exemplary embodiment consistent with the present invention, deposition of the plasmonic nanoparticle(s) on the equator region of the microresonator may be accomplished using carousel forces (See, e.g., the article, S. Arnold, D. Keng, S. I. Shopova, S. Holler, W. Zurawsky, and F. Vollmer, *Optics Express*, 17, 6230 (2009)). This technique, referred to as "Light Force Functionalization" (or "LFF"), can be used to guide plasmonic nanoparticles to the equator region, where the plasmonic nanoparticles can adhere. (See, e.g., the '363 application.)

The detection signal increase due to the additional plasmonic nanoparticle(s) can be estimated as follows. For simplicity, suppose that the WGM is the lowest order transverse electric ("TE") mode with an approximately Gaussian shaped intensity profile having a breadth of a few microns around the equator (standard conditions). Under this assumption, the WGM "bathes" the plasmonic nanoparticle in a nearly uniform field. Excitation of the dipole resonance of the plasmonic nanoparticle 110 with modal field amplitude $E_0$ generates hot spots slightly above and below the equator 106 as depicted in the detail in FIG. 2. A dielectric target (e.g., a target nanoparticle) is easily caught at one of these spots due to enhanced gradient forces. (See, e.g., the articles, A. Ashkin, J. M. Dziedzic, J. E. Bjorkholm, S. Chu, *Opt. Lett.* 11, 288 (1986), and L. Novotny, R. X. Bian, X. S. Xie, *Phys. Rev. Lett.* 79, 645 (1997), each incorporated herein by reference.) Since the hot spots are part of the local field of the plasmonicly modified composite microresonator, the frequency of the resonator will undergo an enhanced shift as a target particle binds or is adsorbed to the plasmonic particle compared with when a target particle binds or is adsorbed to the bare resonator. Based on the RSP, the resonance enhancement ($R_E$) is produced by the relative increase in polarization energy of a target (analyte) particle at a hot spot over that in the absence of the plasmonic nanoparticle. Consequently $R_E$ can be estimated from the ratio of the intensity at the hot spot to the intensity in the same region in absence of the plasmonic nanoparticle (See e.g. the article Katsuaki Tanabe "Field Enhancement around Metal Nanoparticles and Nanoshells: A Systematic Investigation", *J. Phys. Chem.* C2008, 112, 15721-15728). Referring to FIG. 2, suppose that an extremely small particle 120 of radius $a_d$ (e.g. a protein) is drawn to the top (T) of the plasmonic nanoparticle 110 of radius $a_p$. In such a case, the enhancement $R_E$ can be simply written as:

$$R_{E,max} \approx \left| 1 + 2\left(\frac{1}{1+a_d/a_p}\right)^3 \left(\frac{\varepsilon_p - \varepsilon_m}{\varepsilon_p + 2\varepsilon_m}\right) \right|^2 \quad (2)$$

where $\in_p$ and $\in_m$ are the relative permittivity of the plasmonic nanoparticle (e.g. gold or silver metal) and medium (e.g., water), respectively.

In arriving at Equation (2), it was assumed that the target (dielectric nanoparticle) 120 is considerably smaller than the plasmonic nanoparticle 110, in which case spatial variations of the field within the target 120 can be ignored. It was also assumed that both particles 110,120 are positioned close enough to the resonator surface to avoid including the slight fall off in the evanescent intensity between the microsphere surface and the plasmonic nanoparticle 110 centers. In addition, it was assumed that the binding potential between the image dipole in the plasmonic nanoparticle 110 and the induced dipole in the target dielectric nanoparticle 120 is not significant. To estimate the potential effect associated with "parking" a target protein on a homogeneous plasmonic nanoparticle, it may be assumed that $a_d/a_p \approx 0$. If $\in_p = \in_m$, the enhancement disappears (i.e., $R_E=1$). On the other hand, for a perfect metal (for which $\in_p$ has an infinite magnitude), $R_E=9$. Both estimated enhancements ($R_E$) are reasonable results. (See, e.g., J. R. Reitz, F. J. Milford, R. W. Christy, *Foundations of Electromagnetic Theory* 3rd Edition, (Addison-Wesley, Reading, Mass., 1980), incorporated herein by reference.)

More interestingly, at the dipole plasmonic resonance frequency $\omega_1$, where the real part of the of the metallic permittivity is controlled by the medium (i.e., $R_e[\in_p(\omega_1)]=-2\in_m=-3.5$ for water), the enhancement ($R_E$) is limited principally by the $I_m[\in_p(\omega_1)]$. For a solid gold nanoparticle in water (See, e.g., the article, P. Stoller, V. Jacobsen, V. Sandoghdar, *Opt. Lett.* 31, 2474 (2006), incorporated herein by reference) at resonance$I_m[\in_{pg}(\omega_1)] \approx 2$. This provides an enhancement $R_{Eg} \approx 37$. The enhancement ($R_E$) should be substantially greater for silver because $I_m[\in_{ps}(\omega_1)]$ is considerably smaller than in gold (0.7 vs. 2). Indeed, the enhancement for a solid silver nanoparticle is estimated to be 234.

Before describing some experimental results using a microsphere enhanced with one or more plasmonic nanoparticles (also referred to more generally as a "composite microresonator"), it is useful to review the frequency shift limit associated with adsorption of a target particle on a plain silica microsphere in order to establish a useful benchmark. Referring back to FIG. 1 (and ignoring the plasmonic nanoparticle 110), in known microsphere sensors, sensitivity to each "captured" target entity may vary depending on the location 109 on the microsphere surface that the target entity is adsorbed or captured (e.g., by the target receptors). In general, the microsphere sensor may require that a number of target entities be adsorbed or captured by the target receptors in order to detect (produce a signal greater than the noise), quantify, and/or identify the target (or unknown) entity.

By restricting one or more plasmonic nanoparticles 110 (e.g., provided with target receptors) to the highest sensitivity equator region 106/108, the enhanced WGM sensors, fabricated in a manner consistent with the present invention, can be used to bring each target entity to the plasmonic nanoparticle (and perhaps captured by a target receptor on the plasmonic nanoparticle) and facilitate detection and/or identification on a single target entity particle.

A frequency shift in a resonance mode, due to the adsorption or capture of a target (or unknown) entity, may be detected by a detector (not shown) positioned at the end of the tapered fiber 104.

§4.2 Exemplary Fabrication of a Plasmonicly Enhanced Microsphere Sensor

The '363 publication describes the "carousel trapping" of nanoparticles (e.g., polystyrene (PS) nanoparticles) in a solution in which a resonance is induced in a WGM resonator. Basically, a nanoparticle may be trapped in a radial potential well defined by the combination of two exponential forces—a long-range attractive interaction (believed to be caused by the light resonating within the resonator), and a short-range repulsive interaction (electrostatic interactions). In the '363 publication, the trapped PS nanoparticle may be driven along the high intensity equator region until the local charge will allow attractive interaction. Exemplary embodiments consistent with the present invention exploit this carousel trapping to attach a plasmonic particle (as opposed to a PS nanoparticle) to the resonator surface.

Embodiments consistent with the present invention exploit the foregoing "carousel trapping" phenomenon to functionalize an equator region on a WGM resonator surface with one or more plasmonic nanoparticles (which may themselves be functionalized with target receptors). More specifically, a long-range attractive interaction between the light resonating within the resonator and the plasmonic nanoparticles (this attractive interaction is referred to simply as "light force"), can be used to selectively functionalize only the desired equator region (or mode volume) of the resonator with plasmonic nanoparticles. In order to have attractive interaction, the polarizibility of the plasmonic particle should be positive. Only particles with positive polarizability at the excitation wavelength will be pulled close to the resonator. This phenomenon can be used when selecting plasmonic particles with particular properties (positive polarizibilities at the frequency of the excitation light). More specifically, whether or not the plasmonic nanoparticle has a positive polarizability will be a function of the excitation wavelength (i.e., the wavelength of the laser used to excite a WGM within the resonator) and the geometry of the nanoparticle. Thus, the excitation wavelength and the particle geometry can be used to select an appropriate plasmonic nanoparticle. To reiterate, the plasmonic nanoparticles may themselves be functionalized with target receptors, though this is not necessary, particularly if only the size and/or mass of the target is desired.

With the foregoing in mind, an exemplary method 300 for selectively providing one or more plasmonic nanoparticles on a preferred equator region of the surface of a resonator, using light force, is described with reference to FIG. 3. A resonator with properties (e.g., refractive index, radius, etc.) suitable for the intended detection and/or measuring application is selected. (Block 310) The selected resonator is optically (and perhaps mechanically) coupled with an optical waveguide. (Block 320) Plasmonic nanoparticles suitable for the intended detection and/or measuring application are selected. (Block 330) Then, the equator region (or mode volume) of the surface of the resonator is selectively established with the plasmonic nanoparticles. (Block 340) Finally, the non-equator regions of the resonator surface may be passivated (e.g., using a blocking agent) to prevent non-optimal binding to the surface of the resonator (e.g., non-specific binding of non-target entities in regions that would have a minimal, though measurable effect during sensing, as well as non-optimal binding of target entities in such regions, which would result in a non-ideal response). (Block 350) The exemplary sensor fabrication method 300 is then completed. (Node 360)

Referring back to block 310, in a first experimental embodiment, a fused silica microsphere of radius between 30 and 150 micrometers was produced by heating the end of a tapered optical fiber in the focused beam of $CO_2$ laser.

Referring back to block 330, in the first experimental embodiment, gold nanoshells, that have extinction (absorption and scattering) more than 50% in the wavelength range 600-1000 nm were chosen.

Referring back to block 340, in at least some embodiments consistent with the present invention, the equator region (or mode volume) of the surface of the resonator may be selectively established with the plasmonic nanoparticles by (1) immersing the microresonator in a solution including at least a plasmonic nanoparticle (Block 342), and (2) inducing light to evanescently traverse within the microresonator, thereby generating an attractive force between a surface area of the microresonator and the plasmonic nanoparticle(s) in the solution (Block 344), the attractive force being sufficient to attract the plasmonic nanoparticle close enough to a equator region of surface of the microresonator to permit the nanoparticle to be held (e.g., by adsorption or some other chemical force) to the surface area of the microresonator. The system may then be flushed. (Block 346)

Referring back to block 342, in at least some embodiments consistent with the present invention, the solution is a low conductivity solution selected from a group consisting of (A) water, (B) heavy water, and (C) a phosphate buffered saline solution.

Referring back to block 344, a pump laser sourcing light into the optical waveguide may be adjusted (e.g., tuned) so that it stimulates a resonance within the resonator, which will cause a build-up of optical power within the resonator. The evanescent field associated with the WGM will extend into the solution and provide an intensity gradient attractive force that may draw the plasmonic nanoparticle(s) to the surface of the resonator at the preferred equator region.

Referring back to block 350, the non-equator regions of the resonator surface may be passivated using techniques described in the '363 publication. By preventing adsorption to the surface of the resonator, only the plasmonic nanoparticles' surfaces are available for binding. This advantageously results in a large, uniform, detection signal.

Figure 3:
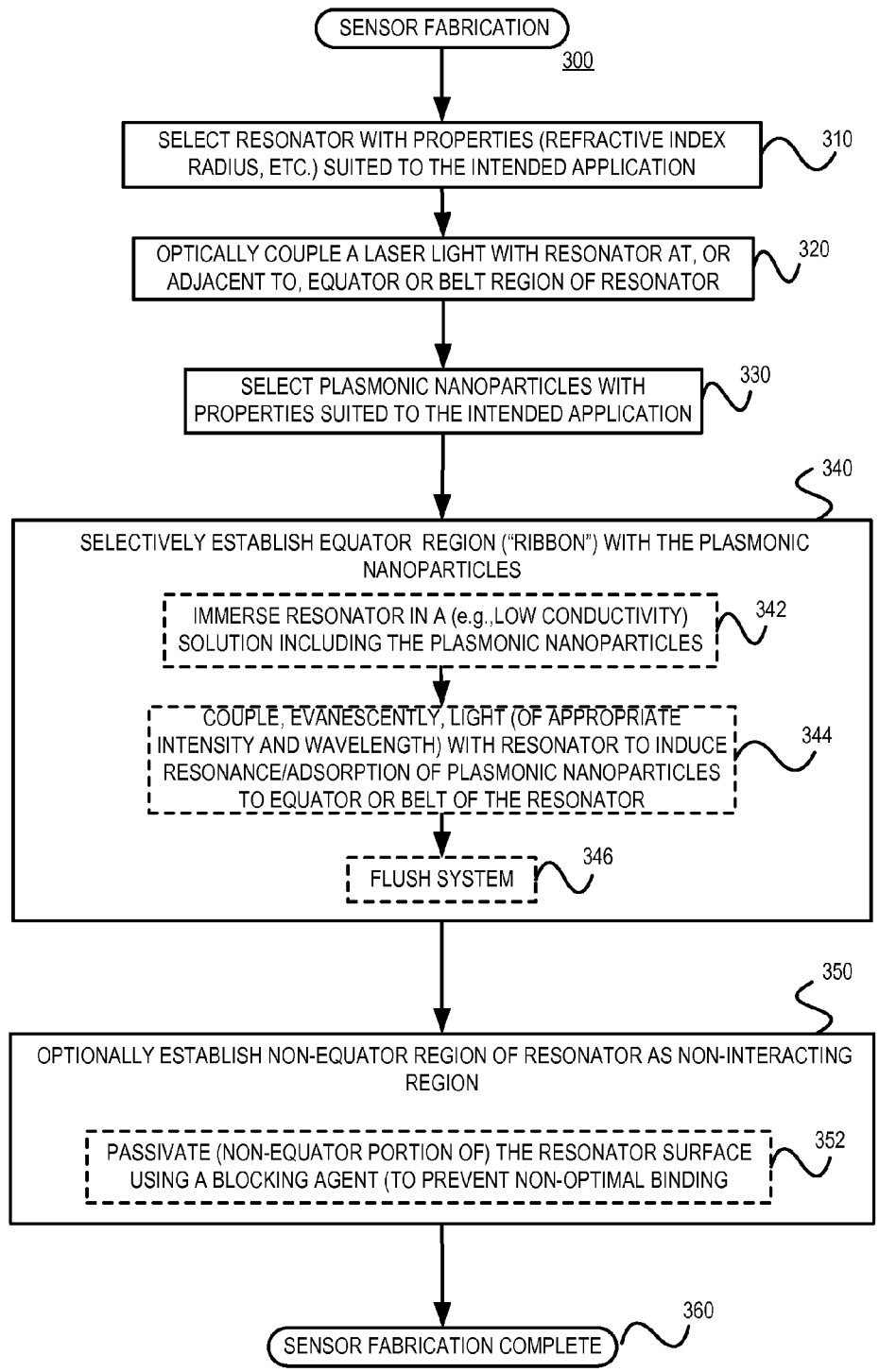
FIG. 3 is a flowchart illustrating an exemplary method for fabricating a plasmonicly enhanced WGM sensor in a manner consistent with the present invention.

Referring generally to FIG. 3, in the first experimental embodiment, the WGM resonator is a fused silica microsphere (R=33.5±0.5 µm) prepared by heating the end of a tapered optical fiber in a focused beam of $CO_2$ laser. The resonator is immersed into a low conductivity solution (e.g., DI water) and enclosed in a 100 µL microfluidic cell. The resonator is brought in contact with a tapered optical fiber, transmitting 632.8 nm light from a tunable laser source to evanescently excite a WGM. This laser is tuned to a resonance of the microsphere resonator having a qualify factor (Q) of $5 \times 10^5$ to $10^6$. Gold nanoshells having extinction (absorption and scattering) more than 50% in the wavelength range 600-1000 nm, dispersed in water in concentration of $\sim 10^6$ particles/ml, are added into the cell. The gold nanoshells have a manufacturer's reported nominal outer radius of 70 nm (Nanospectra Biosciences Inc., lot #NS20080116). Adjusting the power of the pump laser results in a force attracting the gold nanoshells towards the microsphere resonator surface. (The evanescent field associated with the WGM will penetrate into the solution and provide an intensity gradient force that will draw the metal particles to the silica surface). Electrostatic repulsion, in the reach of the double layer near the surfaces, counteracts (at least in part) the attractive force, thereby preventing the fast accumulation of gold nanoshells on the silica surface. Only nanoshells having positive polarizibility at the excitation wavelength can be drawn by the gradient forces. Particles with negative polarizibility, if brought to the surface by other mechanisms (e.g., random walk), produce blue shifts (toward shorter wavelength). At the excitation wavelength, the nanoshells are excited into a dipole/quadrupole plasmonic superposition. A few particles were observed to be drawn to the equator of the resonator by evanescent gradient forces.

The WGM mode of the resonator broadens by 10% to 30% upon adsorption of a single nanoshell. After visual observation of light scattering revealed three binding events in one experiment (and observing step-like changes (shift and broadening and/or splitting) in the resonant dip caused by one or few particles bind on the surface), the microfluidic cell was rinsed with DI water for a sufficient period (e.g., ~2 minutes) to eliminate all unbound gold nanoshells from solution. Previously bound gold nanoshells appeared to remain on the surface of the microsphere resonator. The cell was then filled with phosphate buffered saline solution ("PBS") and left for a few minutes to establish a zero accumulation signal.

Naturally, other fabrication methods with other acts, for example growth of one or more plasmonic nanoparticle of particular size and shape, can be used. Further, other materials (e.g., for the resonator, for the solution, and/or for the plasmonic nanoparticles, etc.), and/or different parameters (e.g., resonator diameter, solution conductivity, laser wavelength, and/or laser intensity, etc.) may be used (e.g., depending on the target entity to be sensed).

§4.2.1 Characteristics of First Experimental Embodiment

A plasmonic parking (i.e., when a target "parks" on a plasmonic nanoparticle (provided within the mode volume of a microresonator, for example, on the surface of the microresonator at the equator region, or within the microresonator at the equator region) effect of the first experimental embodiment was tested using dielectric target nanoparticles of about 55 nm (which is a lot larger than proteins of about 3 nm) in order to establish a benchmark. The optimal frequency shift of a bare silica microsphere occurs when a nanoparticle is deposited at the equator where the WGM field is greatest. For an equatorial TE WGM of a microspherical resonator of radius R=33.5 µm, the RSP (Equation (1)) has been evaluated (See, e.g., the articles, S. Arnold, R. Ramjit, D. Keng, V. Kolchenko and I. Teraoka, *Faraday Discuss.*, 137, 65-83, discussion 99-113 (2007), F. Vollmer, S. Arnold, and D. Keng, *Proc. Natl. Acad. Sci.*, USA 105, 20701 (2008), and S. I. Shopova, R. Rajmangal, Y. Nishida, S. Arnold, *Rev. Sci. Inst.*, 81, 103110 (2010), each incorporated herein by reference) for a nanoparticle binding to the equator and predicts a wavelength shift for a 60 nm polystyrene ("PS") particle of 30 fm.

To determine the extent of the predicted plasmonic enhancement, the equator of a microsphere was functionalized with plasmonic particles, (gold nanoshells). The resonator response in the presence of dielectric nanoparticles was then monitored. The experimental results substantially exceeded the benchmark set by RSP.

More specifically, in the experiment, a PBS dispersion of PS nanospheres with mean radius (60 nm) reported by the manufacturer (Polysciences) at a concentration of 60 fM was added to the cell filled with PBS that had been left for a few minutes to establish a zero accumulation signal. The adsorption of PS nanoparticles on the plasmonicly modified microsphere surface results in multiple steps of the resonant wavelength that clearly separate into two groups as shown in the histogram in FIG. 4. The first (left) group consists of steps with a wavelength shift having a most probable value at 30 fm consistent with the shift obtained from RSP (30 fm) using the mean radius (60 nm). Thus, the first group is likely due to adsorption on the microsphere's surface (outside the equator region). The second (right) group consists of considerably larger wavelength shift steps (up to 216 fm). The second group is likely due to adsorption on one or more gold nanoshells. This represents an approximately fourfold enhancement from the largest wavelength shift in the first group (47 fm). The shifts associated with adsorption and desorption of dielectric particles caused less that 2% change in the resonance width. FIG. 5 shows a typical example of the binding data that includes a large step associated with the second group along with smaller steps associated with the first group.

In other experimental embodiments in which the microsphere quality factor, before introducing the plasmonic particles, is on the order of $10^7$ the attachment of a plasmonic particle to the resonator surface produced a splitting of the resonant dip. The split is a result of the hybridization of the mode structure and can only be observed if the width of the resonant mode, before addition of a particle in the resonator's equatorial region, is smaller than the splitting caused by the particle. (See W. Kim, Ş. K. Özdemir, J. Zhu, L, Yang, Appl. Phys. Lett. 98, 141106 (2011) for the conditions for observing mode splitting in water). In one of such experiments the composite resonator consists of dielectric microsphere (radius of 125 µm) and a gold nanoshell. It was found experientially that the ratio of branches of the split dip (shown in FIG. 8B) changes in steps upon adsorption of individual small polystyrene particles (80 nm in diameter) on the surface of the gold nanoshell. Such steps correspond to the simultaneous step-like changes in the splitting between branches (similar as described in W. Kim, Ş. K. Özdemir, J. Zhu, L, Yang, Appl. Phys. Lett. 98, 141106 (2011), but exhibit much better signal to noise ratio. FIG. 8B compares the ratio of the branches' relative intensity and the split distance of the branches of the mode as dielectric particles arrive on the plasmonic particle. Although there is a correlation between the two sets of data, the ratio data has significantly better signal to noise characteristics. This implies better limit of detection (LOD).

§4.2.2 Finite Element Method Simulation

Figure 4:
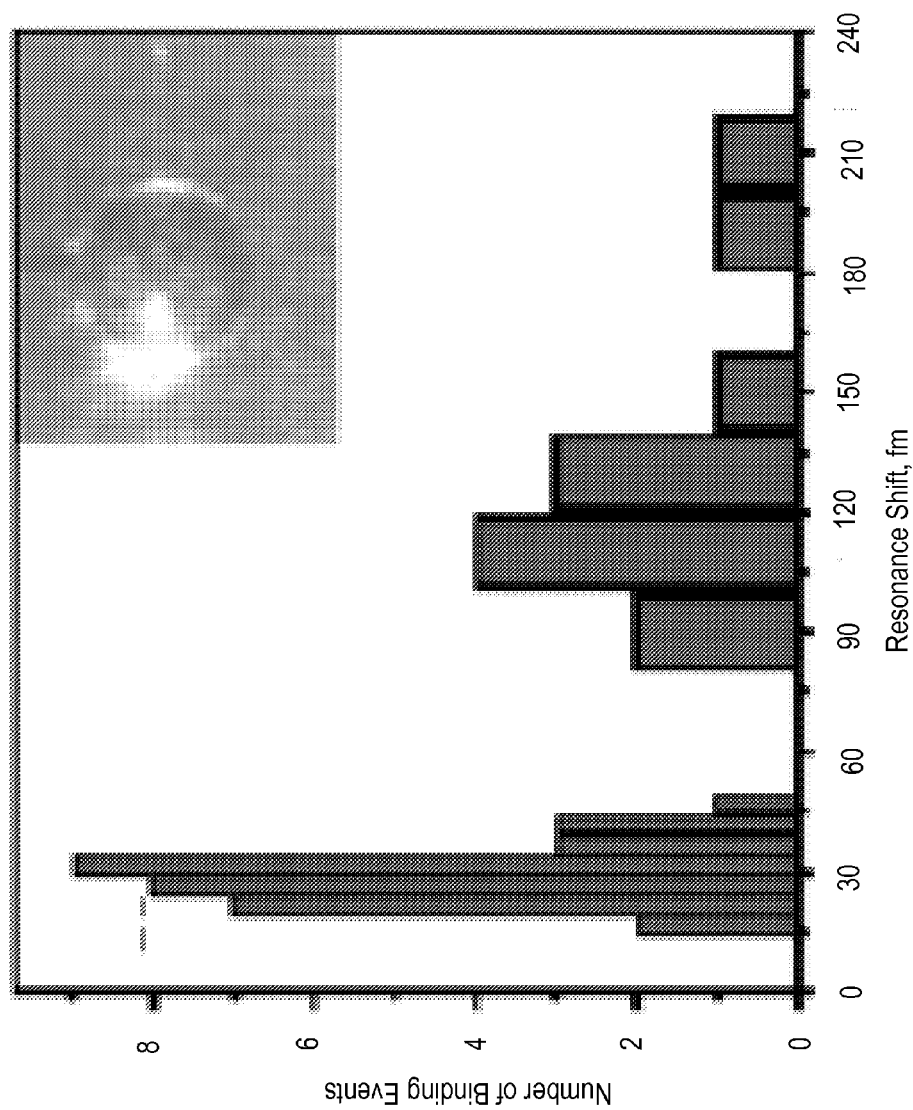
FIG. 4 illustrates resonance shift statistics for an experimental WGM resonator having gold nanoshells provided at its equator region, which is exposed to polystyrene ("PS") particles.
Figure 5:
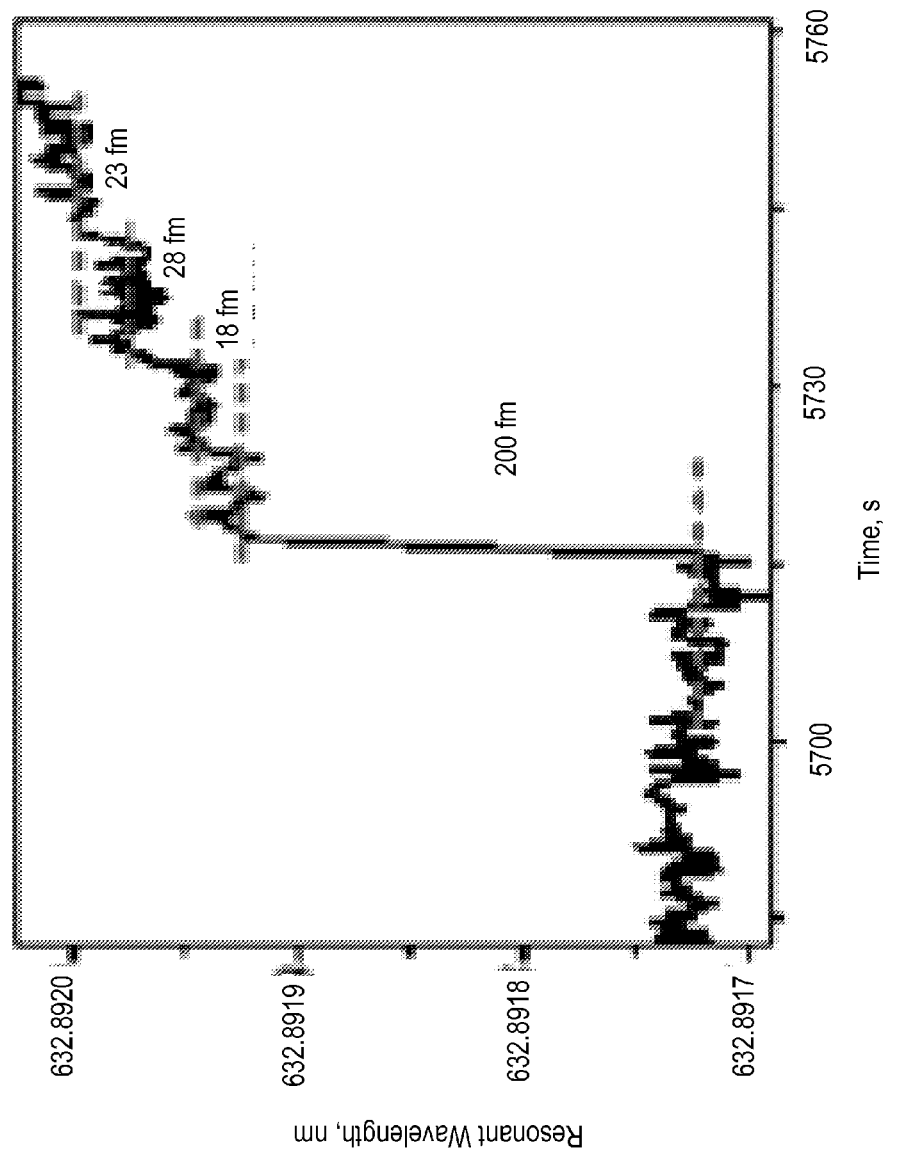
FIG. 5 illustrates wavelength shift data of the experimental WGM resonator.

To help understand the second (right) group in FIG. 4, the local intensity that would be seen by the dielectric particles as each parks on a plasmonic hot spot was simulated. At the wavelength used, a gold nanoshell of nominal size would be primarily excited into a quadrupole mode, as shown in the Finite Element Method (FEM) simulation seen in FIG. 6. The four lobes of this field have intensities that drop off very rapidly. A parking place for the 55 nm radius dielectric sphere that should lead to optimal field overlap is seen.

§4.2.3 Discussion of Detection Limit Using a Model Consistent with Experimental Results As the following discussion is largely theoretical, it should not limit the scope of the present invention. It is important (for our scientific understanding of the physical phenomena) to determine the magnitude of the influence on the WGM of a plasmonically parked dielectric particle (i.e., a target particle "parked" on a plasmonic nanoparticle provided in the equator region of a microresonator), in comparison with the same particle that binds directly to the silica surface. This determination can be made by calculating the ratio of the excess polarization energy of the dielectric particle (i.e., the target) at a plasmonic hot spot to that at the silica surface in the presence of the same WGM. Since the quadrupole lobe penetrates into a small portion of the target nanoparticle, a simple dipole approximation (as used on the silica surface) is not used. Instead, the excess polarization energy in each case is represented more generally by numerically constructing the integral of $\Delta \in E_b \cdot E^*_a /2$ over the nanoparticle's volume, (See, e.g., the text, J. R. Reitz, F. J. Milford, R. W. Christy, *Foundations of Electromagnetic Theory* 3rd Edition, (Addison-Wesley, Reading, Mass., 1980), incorporated herein by reference) where $\Delta \in = \in_d - \in_m$, with $\in_d$ being the relative permittivity of the dielectric particles, and $E_b \cdot E^*_a$ being the product of the field before the particle insertion with that after the particle insertion. These integrals were computed using FEM simulation data. It was determined that the ratio of (1) the integral evaluated for the particle binding as in FIG. 6 to (2) the integral evaluated for direct binding to the equator of the microresonator is 3.1. This ratio value is in good agreement with the experimentally found enhancement of ~4.

Figure 6:
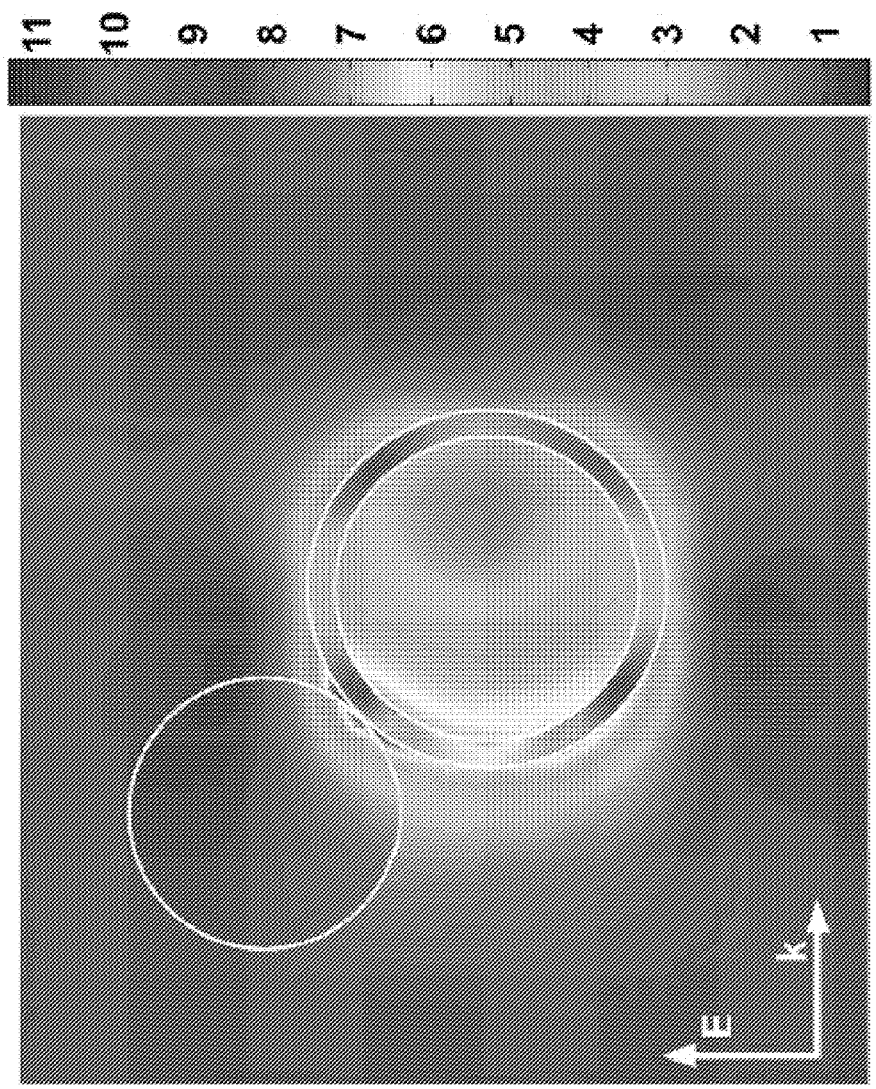
FIG. 6 illustrates a FEM simulation of the "parking" of a PS sphere at one of the forward quadrupole lobes of a plasmonic nanoshell.

FIG. 6 illustrates that the penetration depth of the field into the dielectric target particle from the gold nanoshell(s) is far smaller than the target particle's radius. This greatly reduces the enhancement, since only the small sliver of material near the contact interface is actually significantly polarized. Consequently, as target particle sizes are reduced to the size of an MS2 virus (radius≈12 nm) or a Polio virus (radius≈15 nm), the enhancement should increase (and indeed it does). By using the same FEM approach for the MS2 virus positioned on a quadrupole lobe as in FIG. 6, an enhancement of 16.5 at the quadrupole resonance (649 nm) was computed (even though the field is found to be only partially penetrating). Extending this simulation to a single protein such as BSA (radius≈3 nm), the computed enhancement increases to 37.3.

A better place to look for greater enhancements is at a dipole resonance. For the same nanoshells as in FIG. 6, the dipole should be reached at 810 nm and produce an intensity pattern similar to that in FIG. 2 (i.e., two lobes). Since the dipole near field falls off much more slowly than the quadrupole field, overlap between the field and the target particle's dielectric form is improved. The net effect is that the enhancement for an MS2 virus falling into a dipole lobe is 101.0. For BSA, the enhancement is even higher at 199.0.

§4.3 Target Detection/Measurement Methods

Figure 7:
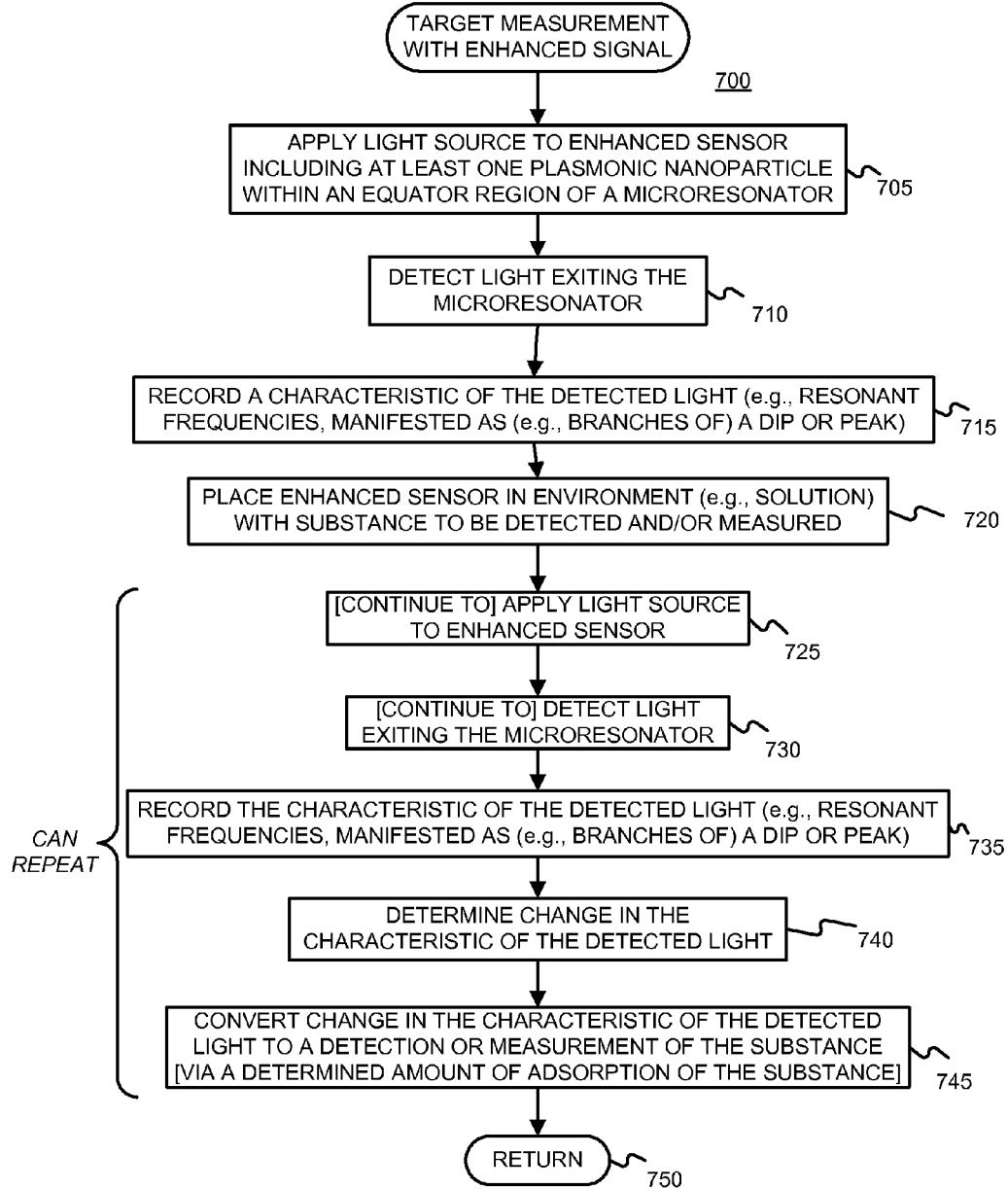
FIG. 7 is a flow diagram of an exemplary method, consistent with the present invention, for using a plasmonicly enhanced sensor consistent with the present invention to detect the presence or amount of a target entity.

FIG. 7 is a flow diagram of an exemplary method 700, consistent with the present invention, for using an plasmonicly enhanced sensor consistent with the present invention to detect the presence or amount of a target entity. A light source is applied to the plasmonicly enhanced WGM biosensor. (Block 705) Light exiting (e.g., scattered out from) the microresonator is detected. (Block 710) A characteristic of the detected light (e.g., resonant frequencies, manifested as a peak or dip (or branches of a split peak or dip)) is recorded. (Block 715)

The plasmonicly enhanced sensor is then placed into an environment (e.g., solution) with substance to be detected and/or measured. (Block 720) The tunable light source is (e.g., continues to be) applied to the plasmonically enhanced sensor (Block 725) through an waveguide, and light exiting the plasmonically enhanced sensor, coupled to the waveguide, is (e.g., continues to be) detected (Block 730). The characteristic of the detected light (e.g., resonant frequencies, manifested as a peak or dip (or branches of a split dip or peak) is again recorded. (Block 735) A change in the characteristic of the detected light is then determined. (Block 740) Finally, the change in the characteristic of the detected light is converted to a detection or measurement of the target (Block 745) before the method 700 is left (Node 750).

Referring back to blocks 715, 735 and 745, in a first exemplary method, the characteristic of the detected light recorded may be a dip corresponding to a resonance frequency, and the difference in the resonance frequencies (i.e., the shift in the resonant frequency) may be used to determine the presence or amount of the target.

Figure 8A:
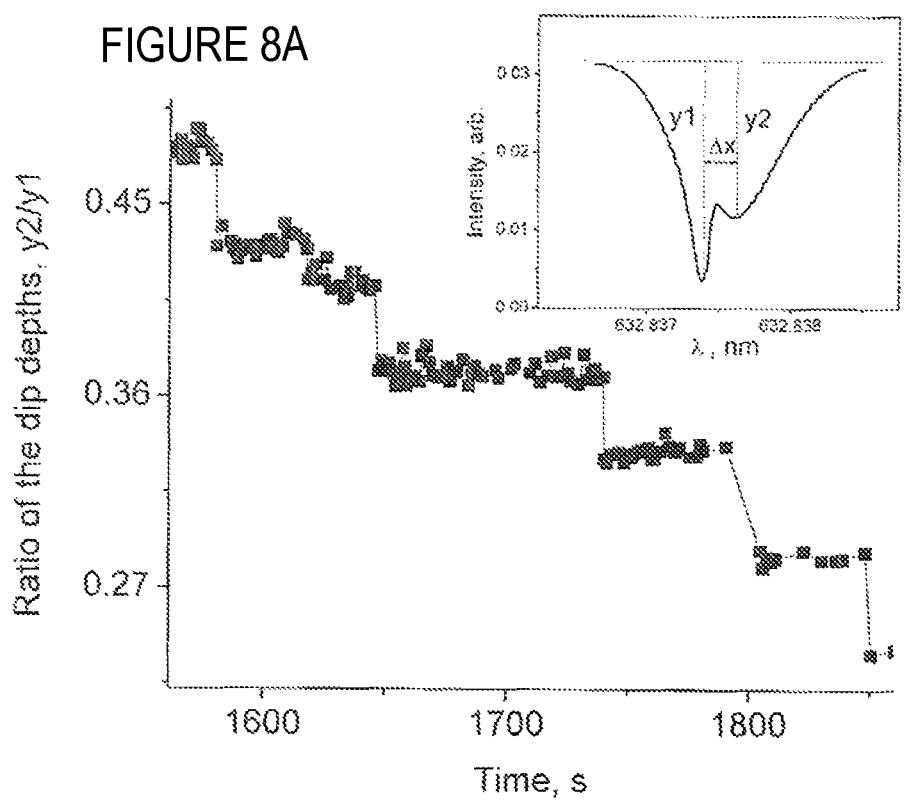
FIG. 8A illustrates steps in a ratio of resonance dip depths in a split mode of an experimental plasmonicly enhanced sensor.
Figure 8B:
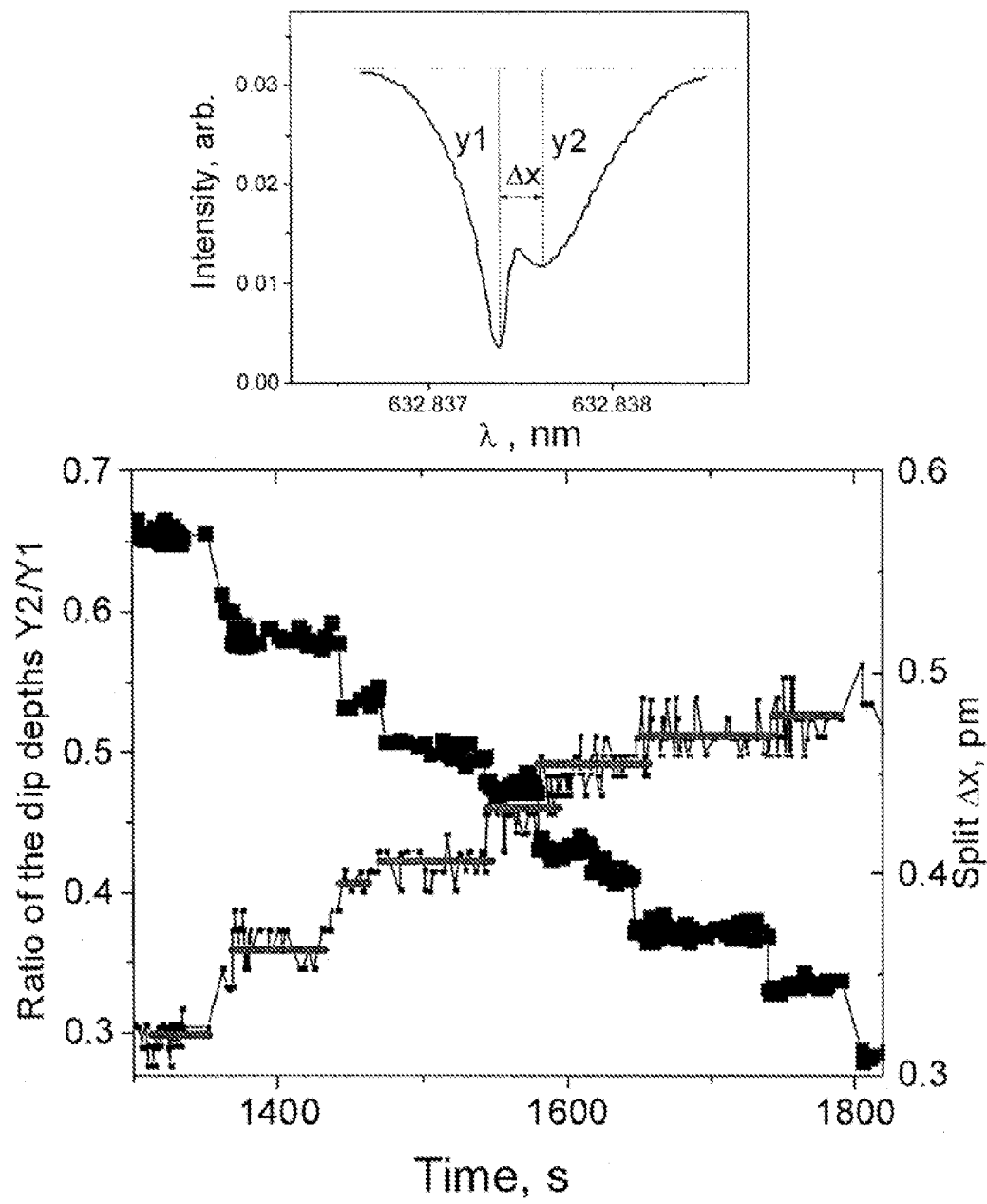
FIG. 8B compares the ratio of resonance dip depths in a split mode, with the distance between the two branches of the split resonance dip.

Again, referring back to blocks 715, 735 and 745, as well as FIG. 8 (which illustrates steps in a ratio of branch depths of a split resonance dip in an experimental plasmonicly enhanced sensor), in a second exemplary method, a split dip waveform is detected and a change in the ratio of the branch depths (y2/y1) is used to determine the presence or amount of the target. In such a second exemplary method, a first waveform representing a benchmark resonance frequency in which the composite resonator is free of the target entity (the first waveform including a first pair of split resonant dips) is identified from the light exiting the microresonator at a first time. (Recall block 715.) A second waveform shape indicating the adsorption of the target entity to at the composite resonator (the second waveform including a second split resonant dip) is identified from the light exiting the composite resonator at a second time (which is after the first time). (Recall block 735.) Finally, a ratio of depths of the branches of the first split resonance dip of the first waveform is compared with a ratio of depths of the branches of the second split resonance dip of the second waveform to determine the presence or amount of the target. (Recall, block 745.)

Figure 9:
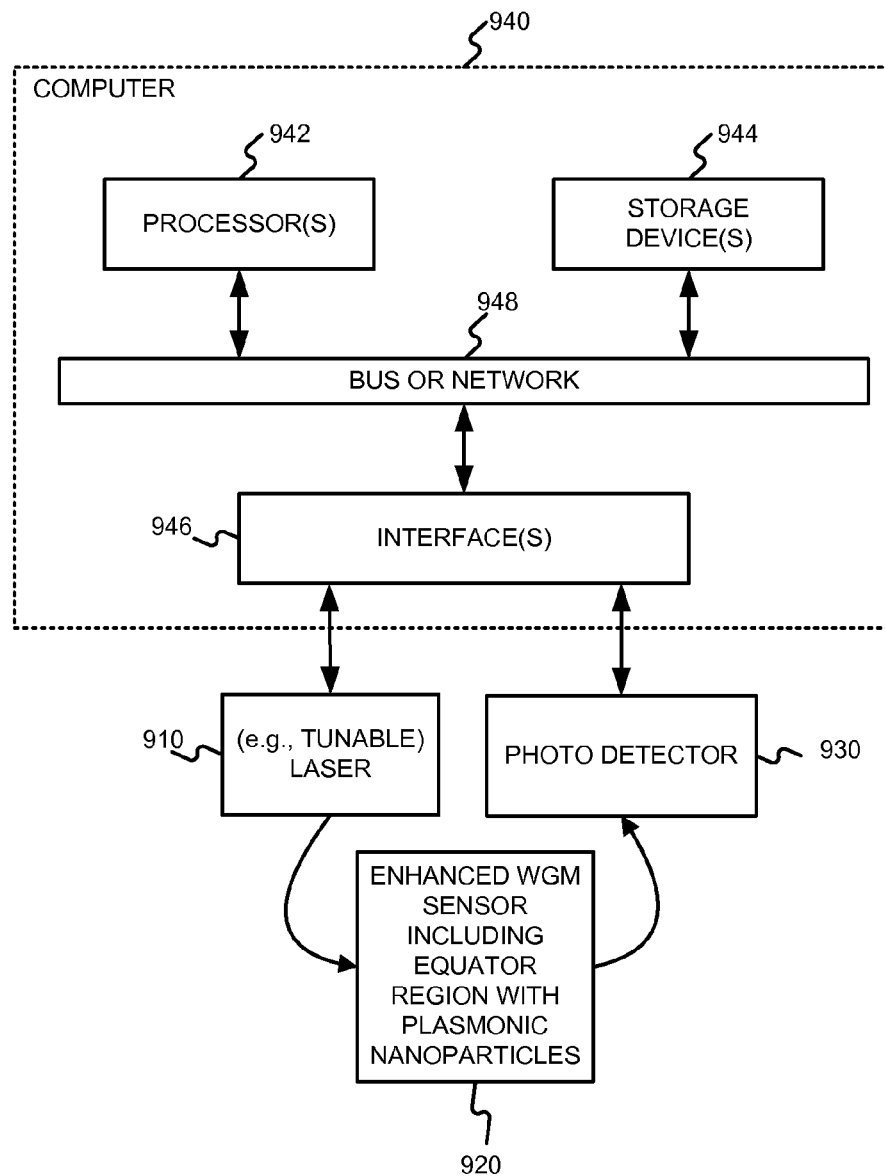
FIG. 9 is a block diagram of an exemplary detection system which may use a plasmonicly enhanced WGM sensor in a manner consistent with the present invention.

§4.4 Exemplary System in which the Plasmonicaly Enhanced WGM Sensor May be Used FIG. 9 is a block diagram of exemplary sensor detection system 900 which may use the plasmonicly enhanced WGM sensor for detecting, measuring, and/or identifying target entities such as biomolecules (e.g. proteins, virus particles, etc.). The sensitivity of the WGM sensor 920 has been enhanced over known systems such that small entity, down to the size of a protein molecule (~3 nm), detection and identification are possible. Naturally, less sensitive WGM sensors fabricated in a manner consistent with the present invention may be used.

Sensor detection system 900 may include a laser 910, a plasmonicly enhanced WGM sensor 920, an optical waveguide (indicated by arcs), an optical detector, such as a photo detector 930, and a computer system 940. The computer system 940 includes at least one processor 942, at least one storage device 944 (e.g., RAM, ROM, flash memory, computer readable storage medium, etc.), at least one interface 946, and at least one bus or network 948 over which the various elements may interchange data and information.

The tunable laser 910 may be controlled to emit light (of an appropriate wavelength and intensity) into or through the plasmonically enhanced WGM sensor 920, via a waveguide. Photo detector 930 may detect light from the WGM sensor 920, via a waveguide. The evaluation of changes in signal output from photo detector 920 may be used to determine the existence of, or the amount of, a target entity that is parked on the plasmonic nanoparticle(s) (or received by target receptor(s) functionalized on the plasmonic nanoparticle(s)) of the WGM sensor 920. In systems 900 including a computer 940, the processor(s) 942 under the direction of routines in memory 944, may control the laser 910 through an interface(s) 946. The processor(s) 942 may receive output signaling from photo detector 930 through an interface(s) 946 and process the signaling to determine the existence, and/or amount, of the target entity sensed.

The plasmonicly enhanced WGM sensor 920 may have any of a number of possible configurations including a single plasmonicly enhanced microresonator sensing head, a multiple plasmonicly enhanced microresonator sensing head using different receptors on different microresonators, and a multiple plasmonicly enhanced microresonator sensing head including at least one plasmonicly enhanced microresonator without receptors to be used to characterize and remove common mode noise. (See, e.g., the '491 patent.)

In some embodiments, the sensor detection system 900 may be implemented using one or more modules. Such modules may be implemented using software, hardware, or a combination of software and hardware.

One exemplary system may correspond to that described with reference to FIG. 4 of the '363 publication, provided with a plasmonically enhanced sensor consistent with the present invention.

§4.5 Refinements, Alternatives, and Extensions

Although exemplary embodiments consistent with the present invention describe fabricating microsphere sensors, the light force functionalization fabrication technique may be used to functionalize the equator regions (or mode volumes) of other configurations of WGM sensors such as, for example, (micro-)cylinders, (micro-)capillaries, (micro-)bubbles, (micro-)disks, (micro-)rings, (micro-)racetrack, (micro-)bottle resonator and (micro-)toroids (or any other resonator geometry that can support a WGM) with plasmonic nanoparticles. Another alternative is to grow the plasmonic nanoparticles on the equator region (or inside the mode volume) of the microresonator.

Although the resonator was described as being silica or amorphous sapphire, other materials for a resonator such as glass, silicon, silicon nitride, silicon oxynitride, gallium nitride (GaN), gallium arsenide (GaAs), indium arsenide (InAs), etc., may be used in a manner consistent with the present invention. Various chemical processes, known to those skilled in the art, may be performed to allow the attachment of target receptors to the resonator.

Although some exemplary embodiments described above used tapered optical fiber to evanescently couple light to the microresonator, other optical waveguides (such as, for example, eroded fiber, lithographed waveguide, rib waveguides, channel waveguides, nanowires, and other structures (or media) capable of supported a guided wavemode (or of guiding electromagnetic modes) may be used instead.

In at least some exemplary embodiments consistent with the present invention, the microresonator may have a diameter of between 30 to 150 μm, though resonators having other diameters may be used.

"Target receptor" is meant to describe any bio-nanoparticle or macromolecule (e.g., virus, protein, polynucleotide, polysaccharide, etc.) that can be attached to a plasmonic nanoparticle and receive a target entity of interest. Target receptors are intended to include numerous bio-nanoparticles and chemical classes, but will typically be organic molecules, or small organic compounds. Target receptors may include any functional groups (e.g., an amine, a carbonyl, a hydroxyl, a carboxyl group, sulfonyl, etc.) necessary for structural interaction (e.g., covalent bonding, hydrogen bonding, etc.) with target entities (e.g., proteins, antibodies, virus, etc.). Target receptors may include, for example, cyclical carbon or heterocyclic structures and/or aromatic or polyaromatic structures substituted with one or more of the above functional groups. Thus, target receptors may include biomolecules such as proteins, peptides, nucleic acids, saccharides, fatty acids, steroids, purines, pyrimidines, derivatives, and structural analogs or combinations thereof.

Target receptors can be obtained from a wide variety of sources including, for example, libraries of synthetic or natural compounds. Numerous means are available for random and directed synthesis of a wide variety of organic compounds and biomolecules, including expression of randomized oligonucleotides. Alternatively, libraries of natural compounds in the form of bacterial, fungal, plant and animal extracts are available to, or readily produced by, those skilled in the art. Additionally, natural or synthetically produced libraries and compounds may be modified through conventional chemical, physical and biochemical means. Known pharmacological agents may be subjected to directed or random chemical modifications, such as acylation, alkylation, esterification and/or amidification to produce structural analogs.

In some embodiments consistent with the present invention, the laser wavelength was _633 or 780 nm, and has a drive power of between 50 and 2000 μW, Naturally, other laser wavelengths and drive powers may be used.

As used in this application (and as generally understood in the art), a "protein" includes at least two covalently attached amino acids, which includes proteins polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids.

The target receptors may be naturally occurring proteins, or fragments of naturally occurring proteins. Thus, for example, cellular extracts containing proteins, or random or directed digests of proteinaceous cellular extracts, may be used. In this way libraries of prokaryotic and eukaryotic proteins may be made for screening in the systems described herein. Particularly preferred in this embodiment are libraries of bacterial, fungal, viral, and mammalian (e.g., human) proteins.

In at least some embodiments consistent with the present invention, the target receptors are peptides. The peptides may be digests of naturally occurring proteins as is outlined above, random peptides, or "biased" random peptides. "Randomized" means that each nucleic acid and peptide consists essentially of random nucleotides and amino acids, respectively. These random peptides (or nucleic acids) may be chemically synthesized, and therefore may incorporate any nucleotide or amino acid at any position. The synthetic process can be designed to generate randomized proteins or nucleic acids, to allow the formation of all or most of the possible combinations over the length of the sequence, thus forming a library of randomized bioactive proteinaceous agents.

In at least some embodiments consistent with the present invention, the target receptors may be nucleic acids. "Nucleic acid" or "oligonucleotide" means at least two nucleotides covalently linked together. A nucleic acid will generally contain phosphodiester bonds, although in some cases, as outlined below, nucleic acid analogs are included that may have alternate backbones, comprising, for example, phosphoramide, phosphorothioate, phosphorodithioate, O-methylphophoroamidite, and peptide nucleic acid backbones and linkages. Other analog nucleic acids include those with positive backbones, non-ionic backbones and non-ribose backbones. Nucleic acids containing one or more carbocyclic sugars are also included within the definition of nucleic acids. The ribose-phosphate backbone may be modified to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthanine, hypoxanthanine, isocytosine, isoguanine, and base pair analogs such as nitropyrrole and nitroindole, etc.

As described above generally for proteins, nucleic acids may be naturally occurring nucleic acids, random nucleic acids, or "biased" random nucleic acids. For example, digests of procaryotic or eukaryotic genomes may be used as is outlined above for proteins.

In general, the target receptors are designed to be complementary to a target entity, such that hybridization of the target entities and the target receptors occurs. It is not necessary for this complementarity to be perfect. For example, in the context of nucleic acid sequences, there may be one or more base pair mismatches that will interfere with hybridization between the target entity and the target receptor. However, if the number of mutations is so great that no hybridization can occur under even the least stringent of hybridization conditions, the target entity will not be considered to be complementary to the target receptor. "Substantially complementary" means that the target receptors are sufficiently complementary to the target entities to hybridize under selected reaction conditions.

In some embodiments consistent with the present invention, the target entity may be a "target sequence" which is a nucleic acid sequence on a single strand of nucleic acid. The target sequence may be a portion of a gene, a regulatory sequence, genomic DNA, cDNA, RNA including mRNA and rRNA, etc. The target sequence may be any length, with the understanding that longer sequences are more specific. As will be appreciated by those skilled in the art, the complementary target sequence may take many forms. For example, it may be contained within a larger nucleic acid sequence (e.g., all or part of a gene or mRNA, a restriction fragment of a plasmid or genomic DNA, among others.) Target receptors are made to hybridize to target sequences to determine the presence or absence of the target sequence in a sample.

In at least some embodiments consistent with the present invention, the target receptors may be organic chemical moieties.

In some embodiments consistent with the present invention, linkers may be used to attach the target receptors to the plasmonic nanoparticle, to facilitate good attachment, provide sufficient flexibility to allow good interaction with the target entities, and/or to avoid undesirable binding reactions.

In at least some embodiments consistent with the present invention, the bioactive target receptors are synthesized first, and then attached to the plasmonic nanoparticle(s). As will be appreciated by those in the art, this will be done depending on the composition of the bioactive target receptors and the plasmonic nanoparticle(s).

In some exemplary embodiments consistent with the present invention, the surface of a plasmonic nanoparticle (e.g., an Au nanoshell) can be functionalized by various surface chemistries which provide the desired chemical properties for stable and defined binding of target receptors with high functionality using techniques that have been developed for SPR sensing. (See, e.g., the article, J. Homola, S. S. Yee, G. Gauglitz, "Surface Plasmon Resonance Sensors: Review," *Sensors and Actuators B*, Vol. 54 pp. 3-15, (1999), incorporated herein by reference.) Other exemplary embodiments consistent with the present invention may use a known method utilizing direct and fast covalent attachment of proteins through a homobifunctional cross-linker, 1,4-di-([2-pyridyldithio]propionamido)butane (DPDPB). (See, e.g., the article, V. Mansuy-Schlick, R. Delage-Mourroux, M. Jouvenot, W. Boireau, "Strategy of Macromolecular Grafting onto a Gold Substrate Dedicated to Protein-Protein Interaction Measurements," *Biosensors and Bioelectronics*, Vol. 21, pp. 1830-1837, (2006), incorporated herein by reference.) Other techniques to attach one or more target receptors to one or more plasmonic nanoparticles, such as gold nanoshells for example, may be used.

For resonators with higher Q factors ($>7 \times 10^6$ in water), which are achievable for spheroids of diameters in the range of 100-300 µm, conventional WGM sensors of these sizes are not sensitive to the change in resonant wavelength caused by target nanoparticles smaller than 100 nm. However, by attaching a plasmonic nanoparticle on the surface of such a resonator at the equator region (as described above), embodiments consistent with the present invention create a sensitive spot on the plasmonic nanoparticle. In such composite resonators the resonance dip (peak) is split into two branches and the detection method relies on the changes in the ratio of the relative intensities of the two branches.

The exemplary composite sensors (including a resonator and at least one plasmonic nanoparticle within the mode volume) is unique in its ability to combine double analysis on the same target, WGM single biological/chemical object (virus, large protein molecules) recognition by size and the interaction with a specific antibody, and SERS recognition on a molecular level. That is, different characteristics of the output light are measured. The plasmonicly enhanced WGM biosensor can be used for molecular identification techniques such as surface-enhanced Raman spectroscopy ("SERS"). (See, e.g., the article, Fuller, K A, Smith, D D, "Cascaded Photoenhancement from Coupled Nanoparticle and Microcavity Resonance Effects," *Optics Express*, Vol. 15, pg. 3575 (2007), incorporated herein by reference.) One example in which such analysis would be valuable is the study of the genetic features of HIV virus that persist in the presence of highly active antiretroviral therapy. Although a mutant HIV-I virus might still be recognized by the same antibody, the changes in envelope and pol genes that are making it resistive could be identified by SERS.

Optimizing the shape and size of the plasmonic particles and considering clusters (e.g. dimmers of two plasmonic particles of close proximity) is expected to produce an even larger effect and further reduce the limit of detection.

§4.6 Conclusions

Recently, the LOD for biodetection by WGM devices has been reduced to an equivalent radius of ~17 nm, by using an ultra-low noise laser source for a microsphere having a relatively low $Q \sim 10^6$. (See, e.g., the article, S. I. Shopova, R. Rajmangal, Y. Nishida, S. Arnold, *Rev. Sci. Inst.* 81, 103110 (2010).) Since the wavelength shift of an extremely small particle is proportional to its polarizability (Recall Equation (1).) or volume, an enhancement of 199 in this shift is expected to reduce the detectable radius to ~17 nm/199$^{1/3}$ or 2.9 nm, clearly below the size of the smallest virus and in the range of an intermediate sized protein.

What is claimed is:

1. A method for determining the presence or concentration of a target entity in a medium, the method comprising:
   a) exposing a composite microresonator, including a dielectric microresonator and at least one plasmonic nanoparticle within the mode volume of the dielectric microresonator, to the medium;
   b) inducing light to resonate within the microresonator, thereby
      (1) generating (A) a resonant mode in association with the dielectric microresonator and (B) a plasmonic resonance in the at least one plasmonic nanoparticle, and
      (2) attracting the target entity to at least one plasmonic nanoparticle of the composite microresonator; and
   c) determining the presence, mass, or concentration of the target entity using a change in a characteristic of light exiting the composite microresonator.

2. The method of claim 1 wherein the act of determining the presence of the target entity can detect a target entity having a radius as low as 3 nm.

3. The method of claim 1 wherein the dielectric microresonator has a geometry selected from a group of geometries consisting of (A) micro-sphere, (B) micro-ring, (C) micro-capillary (D) micro-cylinder, (E) micro-racetrack, (F) micro-disk (G) micro-toroid, (H) micro-bottle, and (I) micro-bubble.

4. The method of claim 1 wherein the dielectric microresonator is made of a material selected from a group consisting of (A) silica, (B) glass, (C) silicon, (D) silicon nitride, (E) silicon oxynitride, (F) gallium nitride, (G) gallium arsenide, and (H) indium arsenide.

5. The method of claim 1 wherein the plasmonic nanoparticle has a geometry selected from a group of geometries consisting of (A) nano-shell, (B) nano-rod, (C) non-concentric sphere, and (D) nano-dot.

6. The method of claim 1 wherein the plasmonic nanoparticle consists of dimmers or several plasmonic particles placed in close proximity as a cluster.

7. The method of claim 1 wherein the plasmonic nanoparticle is a metal selected from a group consisting of (A) Au, (B) Ag, (C) Cu, (D) Ti, and (E) Cr.

8. The method of claim 1 wherein the plasmonic nanoparticle is a semiconductor nanocrystal (quantum dot).

9. The method of claim 1 wherein the plasmonic nanoparticle is functionalized with a receptor specific to the target entity.

10. The method of claim 1 wherein the act of determining the presence or concentration of the target entity using a change in a characteristic of light exiting the composite microresonator includes:
    i) identifying, from the light exiting the microresonator at a first time, a first waveform representing a benchmark resonance frequency in which the composite microresonator is free of the target entity,
    ii) identifying, from the light exiting the microresonator at a second time which is after the first time, a second waveform shape indicating the adsorption of the target entity onto the at least one plasmonic nanoparticle, and
    iii) comparing the second waveform with the first waveform.

11. The method of claim 1 wherein the act of determining the presence or concentration of the target entity using a change in a characteristic of light exiting the composite microresonator includes:
    i) identifying, from the light exiting the microresonator at a first time, a first waveform representing a benchmark resonance frequency in which the composite microresonator is free of the target entity, the first waveform including a first split resonant dip or peak having two branches,
    ii) identifying, from the light exiting the microresonator at a second time which is after the first time, a second waveform shape indicating the adsorption of the target entity onto the plasmonic nanoparticle, the second waveform including a second split resonant dip or peak having two branches, and
    iii) comparing the ratio of the relative intensities of the branches of the first split resonance dip or peak of the first waveform with the ratio of the relative intensities of the branches of the second split resonance dip or peak of the second waveform.

12. The method of claim 10 wherein the act of determining the presence of the target entity using a change in a characteristic of light exiting the microresonator further includes simultaneously analyzing spectra of the light exiting the microresonator.

13. The method of claim 12 wherein the act of analyzing spectra uses surface-enhanced Raman spectroscopy (SERS), and wherein a Raman shift is enhanced by the composite microresonator.

14. The method of claim 11 wherein the act of determining the presence or concentration of the target entity using a change in a characteristic of light exiting the microresonator includes further includes analyzing a spectra of the light exiting the microresonator.

15. The method of claim 14 wherein the act of analyzing spectra uses surface-enhanced Raman spectroscopy (SERS).

16. The method of claim 1 wherein the light is induced to resonate within the composite microresonator using an optical waveguide proximal to the microresonator, the optical waveguide carrying a laser light.

17. A method for fabricating a sensor for determining the presence or concentration of a target entity in a medium, the method comprising:
    a) placing a microresonator in a solution including at least one plasmonic nanoparticle;
    b) inducing light to resonate within the microresonator, thereby (1) generating a resonant mode in association with the microresonator, and (2) attracting at least one plasmonic nanoparticle to the mode volume of the microresonator until the at least one plasmonic nanoparticle is adsorbed onto the surface within the mode volume of the microresonator.

18. The method of claim 17 wherein surface areas of the microresonator other than the equator region are substantially free of the nanoparticle.

19. The method of claim 17 wherein the plasmonic nanoparticle is functionalized with a receptor specific to the target entity.

20. The method of claim 17 further comprising:
    c) passivating surface areas of the microresonator other than the equator region.

21. The method of claim 17 wherein the solution is a low conductivity solution selected from a group consisting of (A) water, (B) heavy water, and (C) a phosphate buffered saline solution.

22. The method of claim 17 wherein the microresonator has a geometry selected from a group of geometries consisting of (A) micro-sphere, (B) micro-ring, (C) micro-cylinder, (D) micro-racetrack, (E) micro-disk (F) micro-toroid, (G) micro-bottle, (H) micro-capillary, and (I) micro-bubble.

23. The method of claim 17 wherein the microresonator is made of a material selected from a group consisting of (A) silica, (B) glass, (C) silicon, (D) silicon nitride, (E) silicon oxynitride, (F) gallium nitride, (G) gallium arsenide, and (H) indium arsenide.

24. The method of claim 17 wherein the plasmonic nanoparticle has a geometry selected from a group of geometries consisting of (A) nano-shell, (B) nano-rod, (C) non-concentric sphere, and (D) nano-dot.

25. The method of claim 17 wherein the plasmonic nanoparticle consists of several dimmers or several plasmonic particles placed in close proximity as a cluster.

26. The method of claim 17 wherein the plasmonic nanoparticle is a metal selected from a group consisting of (A) Au, (B) Ag, (C) Cu, (D) Ti, and (E) Cr.

27. The method of claim 17 wherein the plasmonic nanoparticle is a semiconductor nanocrystal (quantum dot).

28. The method of claim 17 wherein the resonator selectively attracts only plasmonic nanoparticles that have positive polarizibilities at the wavelength of the light resonating within the microresonator.

29. A sensor for determining the presence or concentration of a target entity in a medium, the sensor comprising:
   a) an optical waveguide;
   b) a microresonator optically coupled with the optical waveguide such that light within the optical waveguide induces a resonant mode within the microresonator at an equator region; and
   c) at least one plasmonic nanoparticle adsorbed onto a surface area of the microresonator within the equator region such that light inducing a resonant mode within the microresonator also causes a plasmonic resonance in the at least one plasmonic nanoparticle.

30. The sensor of claim 29 further comprising:
   at least one receptor which is functionalized on the at least one plasmonic nanoparticle and which is specific to the target entity.

31. The sensor of claim 29 wherein the microresonator has a geometry selected from a group of geometries consisting of (A) micro-sphere, (B) micro-ring, (C) micro-cylinder, (D) micro-racetrack, (E) micro-disk (F) micro-toroid, (G) micro-bottle, (H) micro-capillary, and (I) micro-bubble.

32. The sensor of claim 29 wherein the microresonator is made of a material selected from a group consisting of (A) silica, (B) glass, (C) silicon, (D) silicon nitride, (E) silicon oxynitride, (F) gallium nitride, (G) gallium arsenide, and (H) indium arsenide.

33. The sensor of claim 29 wherein the plasmonic nanoparticle has a geometry selected from a group of geometries consisting of (A) nano-shell, (B) nano-rod, (C) non-concentric sphere, and (D) nano-dot.

34. The method of claim 29 wherein the plasmonic nanoparticle consists of dimmers or several plasmonic particles placed in close proximity as a cluster.

35. The sensor of claim 29 wherein the plasmonic nanoparticle is a metal selected from a group consisting of (A) Au, (B) Ag, (C) Cu, (D) Ti, and (E) Cr.

36. The sensor of claim 29 wherein the plasmonic nanoparticle is a semiconductor nanocrystal (quantum dot).

37. The sensor of claim 29 wherein the sensor has a limit of detection on the order of 3 nm.

\* \* \* \* \*